United States Patent
Bazan et al.

(10) Patent No.: US 6,653,311 B1
(45) Date of Patent: Nov. 25, 2003

(54) 5-LIPOXYGENASE INHIBITORS: (2-AZINYLAMINO) QUINONE DERIVATIVES

(75) Inventors: Nicholas G. Bazan, New Orleans, LA (US); Carlos Sunkel, Madrid (ES); Julio Alvarez Builla-G., Madrid (ES)

(73) Assignees: Board of Supervisors of Louisiana State University, Baton Rouge, LA (US); Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/179,534

(22) Filed: Jun. 25, 2002

(51) Int. Cl.[7] .................... C07D 401/02; C07D 213/02; A61K 31/44
(52) U.S. Cl. .................... 514/252.1; 514/275; 514/352; 514/242; 514/243; 544/316; 544/336; 544/182; 544/183; 546/312
(58) Field of Search .......................... 546/312; 544/316, 544/336, 182, 183; 514/252.1, 275, 352, 242, 243

(56) References Cited

U.S. PATENT DOCUMENTS

| | | | |
|---|---|---|---|
| 4,393,075 A | 7/1983 | Terao et al. | 424/304 |
| 4,851,413 A | 7/1989 | Terao et al. | 514/277 |
| 4,985,447 A | 1/1991 | Terao et al. | 514/333 |
| 5,106,858 A | 4/1992 | Terao et al. | 514/333 |

FOREIGN PATENT DOCUMENTS

WO    WO 86/04058    7/1986

OTHER PUBLICATIONS

Matsuo et al, Journal of the Physical Organic Chemistry, vol. 7, pp. 567–577, 1994.*
Bazan, N.G. et al., "(2–Azinylamino)quinone Derivatives as 5–Lipoxygenase Inhibitors," a manuscript to be submitted to J. Med. Chem.
Boarland, M.P.V. et al., "Pyrimidines. IV. Experiments on the Synthesis of Pyrimidine and 4,6–Dimethylpyrimidine," J. Chem. Soc., vol 1952, pp. 4691–4695 (1952).
Bruce, J.M. et al., "Benzoquinones and Related Compounds. Part 3. Preparation of 1,4–Benzoquinones by Oxidation of Hydroquinones with Manganese Dioxide," J. Chem. Research (S), vol. 1981, pp. 252–253 (1981).
Burgos, C. et al., "Halogenation Pyridinium–N–(2'–pyridyl)aminide. An Easy Synthesis of Halo–2–aminopyridines," Tetrahedron, vol. 51, pp. 8649–8654 (1995).
Carceller, R. et al., "Azinium–N–(2'–azinyl)aminides: Synthesis, Structure and Reactivity," Tetrahedron, vol. 50, pp. 4995–5012 (1994).
Carceller, R. et al., "Pyridinium–N–(2–pyridyl)aminides: A Selective Approach to Substituted 2–Aminopyridines," Tetrahedron Lett., vol. 34, pp. 2019–2020 (1993).
Chesterfield, J. et al., "Pyrimidines.VIII. Halo– and Hidrazinopyrimidines," J. Chem. Soc., vol. 1955, pp. 3478–3481 (1955).
Crooks, S.W. et al., "Molecules in focus: Leukotriene B4," The Internat. J. Biochem. and Cell Biol., vol. 30, pp. 173–178 (1998).
Denzlinger, C. et al., "Effect of leukotriene receptor antagonists on leukotriene elimination in the rat," Allergy Clin. Immunol., vol. 85, pp. 218 (1990).
Jones, T.R. et al., "Antigen–induced contraction of guinea–pig isolated trachea: Studies with novel inhibitors and antagonists of arachidonic acid metabolites," Br. J. Pharmacol., vol. 95, pp. 309–321 (1988).
Nelson, P.J. et al., "1,2,4–Triazoles, VI. Synthesis of some s–Triazolo[4,3–a]pyrazines," J. Org. Chem., vol. 27, pp. 3243–3248 (1962).
O'Hickey, S.P. et al., "Leukotrienes C4, D4, and E4 enhance histamine responsiveness in asthmatic airways," Am. Rev. Resp. Dis., vol. 144, pp. 1053–1057 (1991).
Ohkawa, S. et al., "Dual Inhibition of Thromboxane $A_2$ Synthetase and 5–Lipogenase with Scavenging Activity Oxygen Species. Synthesis of a Novel Series of (3–Pyridylmethyl)benzoquinone Derivatives," J. Med. Chem., vol. 34, pp. 267–276, (1991).
Rakhit, A. et al., "Pharmacokinetic Screening of o–Naphtoquinone 5–Lipoxygenase Inhibitors," Pharm. Res., vol. 7, pp. 1071–1076 (1990).

(List continued on next page.)

Primary Examiner—Zinna Northington Davis
(74) Attorney, Agent, or Firm—Bonnie J. Davis; John H. Runnels

(57) ABSTRACT

We have synthesized a series of new derivatives of (2-azinylamino) quinone, that have the general formula shown below. Several compounds of this new series of derivatives have been shown to be inhibitors of 5-lipoxygenase, with minimal or no effect on cycloxygenase-1 and 2-(COX-1 and COX-2) activity.

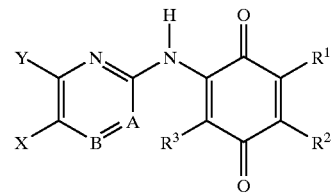

where:
A is N, CH, or, CCl;
B is N, CH, $CCH_3$, or Cph;
X is H, Cl, Br, or I;
Y is H, or $CH_3$;
$R^1$ is H, $CH_3$, $OCH_3$, or Ph; and $R^2$ is H, $CH_3$, $OCH_3$, or Ph; or $R^1$—$R^2$ is $(CH=CH)_2$; and
$R^3$ is H or $CH_3$.

44 Claims, No Drawings

OTHER PUBLICATIONS

Redkar–Brown, D.G. et al., "Inhibition of antigen–induced contraction of guinea pig tracheia by ICI 198,615," Eur. J. Pharmacol., vol. 165, pp. 113–121 (1989).

Sasaki, T. et al., "Nucleophilic Reactions of N–ethoxycabonyliminopyridinium Ylide with a,b–Unsaturated Carbonyl Compounds," Tetrahedron, vol. 28, pp. 1469–1476 (1972).

Shirakawa, K. et al., "Chemotherapeutics XXXIV. Syntheses of some Heterocyclic Hidrazine Compounds and their Action on Tubercle Bacilli," J. Pharm. Soc. Japan, vol. 73, pp. 598–601 (1953).

Smith, L.I. et al., "Quinones and Metallic Enolates XVI. Dibromo–o–xyloquinone and Sodium Malonic Ester," J. Am. Chem. Soc., vol. 64, pp. 528–533 (1942).

Terao, S. et al., "Quinones. Part 2. General Synthetic Routes to Quinone Derivatives with Modified Polyprenyl Side Chains and the Inhibitory Effects of these Quinones on the Generation of the Slow Reacting Substance of Anaphylaxis (SRS–A)," *J. Chem. Soc. Perkin Trans.*, vol. 1, pp. 2909–2920 (1982).

* cited by examiner

5-LIPOXYGENASE INHIBITORS: (2-AZINYLAMINO) QUINONE DERIVATIVES

This invention pertains to a series of new derivatives of (2-azinylamino) quinone, their synthesis, and the use of these derivatives as 5-lipoxygnease inhibitors.

Leukotrienes, identified as 5-lipoxygenase (5-LO) metabolites of arachidonic acid (AA), have been implicated as mediators in a diversity of diseases, including asthma and a number of other inflammatory pathologies, such as rheumatoid arthritis, inflammatory bowel disease, psoriasis and glomerulonephritis. See S. W. Crooks et al., "Molecules in focus: Leukotriene B4," The Internat. J. Biochem. and Cell Biol., vol. 30, pp. 173–178 (1998). Although leukotrienes may not be involved in the initial stages of a disease, they appear to play an important role in the propagation of the disease, by exacerbating the initial, primarily local events and eventually leading to tissue damage.

Through the action of 5-LO, AA is initially oxygenated to give 5-hydroperoxyeicosatetraenoic acid (5-HPETE), which is then transformed by the same enzyme to leukotriene $A_4$ ($LTA_4$). $LTA_4$ is then converted by $LTA_4$-hydrolase to leukotriene $B_4$ ("$LTB_4$"), a potent chemotactic agent that enhances infiltration of leukocytes and their subsequent degranulation. See Crooks et al., 1998. Alternatively, $LTA_4$ can couple to glutathione to produce peptidoleukotrienes (PLTs) $LTC_4$, $LTD_4$ and $LTE_4$ that have profound effects on bronchial and vascular smooth muscle contractility, and promote extensive plasma extravascularization by increasing the permeability of the postcapillary venules. See, e.g., S. P. O'Hickey et al., "Leukotrienes $C_4$, $D_4$, and $E_4$ enhance histamine responsiveness in asthmatic airways," Am. Rev. Resp. Dis., vol. 144, pp. 1053–1057 (1991).

Since the elucidation of the 5-LO biosynthetic pathway, an ongoing debate in drug development has been whether inhibition of the 5-LO enzyme is more efficacious than antagonization of the peptido- or non-peptido-leukotriene receptors. However, evidence suggests that 5-LO inhibitors may be superior to LT-receptor antagonists, since 5-LO inhibitors block the action of the full spectrum of 5-LO products, whereas LT-antagonists produce narrower effects. See D. G. Redkar-Brown et al., "Inhibition of antigen-induced contraction of guinea pig trachea by ICI 198,615," Eur. J. Pharmacol. vol. 165, pp. 113–121 (1989); and T. R. Jones et al., "Antigen-induced contraction of guinea-pig isolated trachea: Studies with novel inhibitors and antagonists of arachidonic acid metabolites," Br. J. Pharmacol., vol. 95, pp. 309–321 (1988). In addition, LT-receptor antagonists appear to prolong the half-lives of LTs by hindering their metabolism. See C. Denzlinger et al., "Effect of leukotriene receptor antagonists on leukotriene elimination in the rat," Allergy Clin. Immunol., vol. 85, pp. 218 (1990).

Numerous attempts have been made in the last decade to identify and develop 5-lipoxygenase (5-LO) inhibitors as therapeutic agents. Among the compounds include several having a 1,4(or 1,2)-quinone moiety. The p-benzoquinone derivative 1 and the o-naphthoquinone 2, with structures as shown below, have been revealed as potent inhibitors of 5-LO. See S. Terao et al., "Quinones. Part 2. General Synthetic Routes to Quinone Derivatives with Modified Polyprenyl Side Chains and the Inhibitory Effects of these Quinones on the Generation of the Slow Reacting Substance of Anaphylaxis (SRS-A)," J. Chem. Soc. Perkin Trans., vol. 1, pp. 2909–2920 (1982); A. Rakhit et al., "Pharmacokinetic Screening of o-Naphtoquinone 5-Lipoxygenase Inhibitors," Pharm. Res., vol. 7, pp. 1071–1076 (1990); S. Ohkawa et al., "Dual Inhibition of Thromboxane $A_2$ Synthetase and 5-Lipoxygenase with Scavenging Activity of Active Oxygen Species. Synthesis of a Novel Series of (3-Pyridylmethyl) benzoquinone Derivatives," J. Med. Chem., vol. 34, pp. 267–276, (1991). See also, U.S. Pat. Nos. 4,393,075; 4,851,415; 4,985,447; and 5,106,858; and of International Application WO 86/04058. The series of(3-pyridylmethyl) benzoquinone derivatives were evaluated for inhibition of thromboxane $A_2$ ($TXA_2$) synthase, inhibition of 5-LO, and scavenging activity of active oxygen species (AOS), and the compound with the structure 3 shown below was the most promising derivative. (Ohkawa et al., 1991).

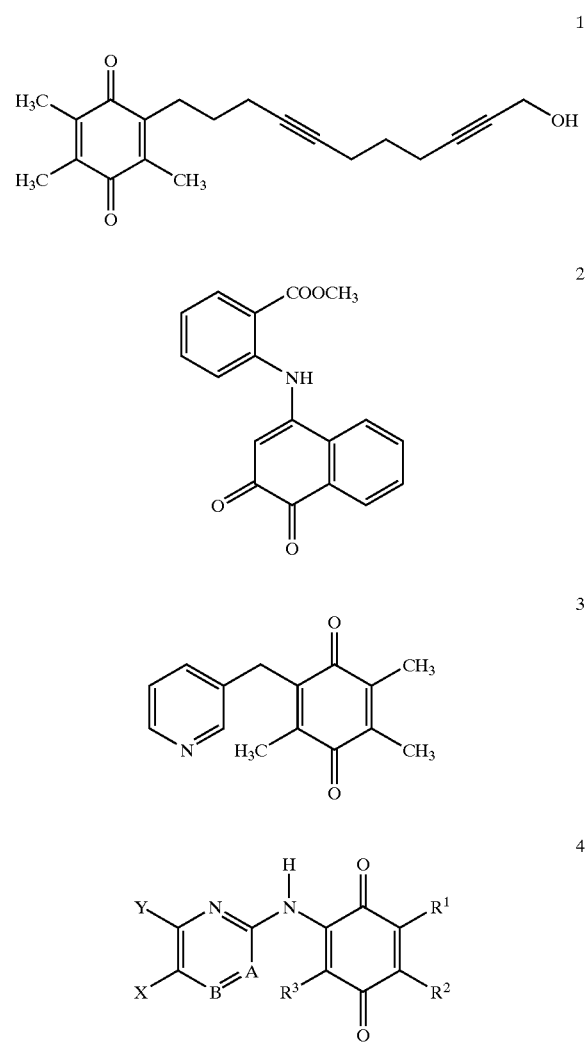

We have synthesized a series of new derivatives of (2-azinylamino)-quinone, structure 4 as shown above. All (2-azinylamino)quinones are antioxidants. Several compounds of this new series of derivatives have been shown to be inhibitors of 5-lipoxygenase, with minimal or no effect on cycloxygenase-1 and 2-(COX-1 and COX-2) activity.

The series of new compounds have the following General Formula 4:

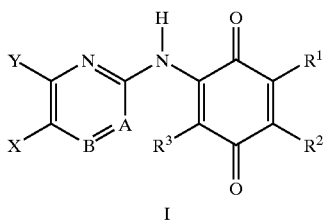

General Formula 4 where:

A is N, CH, or CCl;

B is N, CH, CCH$_3$, or CPh;

X is, H, Cl, Br, or I;

Y is H or CH$_3$;

R$^1$ is H, CH$_3$, OCH$_3$, or Ph; and R$^2$ is H, CH$_3$, OCH$_3$, or Ph; or R$^1$—R$^2$ is (CH=CH)$_2$; and R$^3$ is H or CH$_3$.

Note that in the above formula when R$^1$—R$^2$ is (CH=CH)$_2$, this forms a naphthoquinone having a structure as exemplified below:

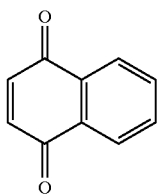

The compounds of General Formula 4 can be used as medication to be administered orally, rectally, topically, parenterally or inhalation, in the form of a pharmaceutical preparation, which contains at least one of the compounds of General Formula 4 in combination with a pharmaceutically acceptable carrier. The pharmaceutical carrier is selected with regard to the intended route of administration and standard pharmaceutical practice. For example, the compounds may be administered orally in the form of tablets containing such excipients as starch or lactose, or in capsules or ovules either alone or in admixture with excipients, or in the form of elixirs or suspensions containing flavoring or coloring agents. They may be injected parenterally, for example, intravenously, intramuscularly, or subcutaneously. For parenteral administration, they are best used in the form of a sterile aqueous solution which may contain other substances, for example, salts or glucose. The amount of active compound is between 0.1 and 99% by weight of the preparation, preferably between 2 and 50% by weight in oral preparations. The daily dose of the active substance depends on the type of administration and, in general, is between 25 and 100 mg if administered orally and between 0.1 and 50 mg per dose if administered intravenously. In clinical practice, the dosage will be adjusted for the particular patient and may vary with age, weight, and response of the patient. The above dosages are exemplary of an average case but can be increased or lowered if merited.

The preparation of the compounds of General Formula 4 is further illustrated by the following examples. In general the compounds were synthesized as shown below by reaction between the aminides 5 and the corresponding quinones 6 to yield the aminoquinones 4a–y (Table 1). The aminides 5a–e were prepared from the corresponding pyridinium salts as previously described. See R. Carceller et al., "Pyridinium-N-(2-pyridyl)aminides: A Selective Approach to Substituted 2-Aminopyridines," Tetrahedron Lett., vol. 34, pp. 2019–2020 (1993); R. Carceller et al., "Azinium-N-(2'-azinyl)aminides: Synthesis, Structure and Reactivity," Tetrahedron, vol. 50, pp. 4995–5012 (1994); and C. Burgos et al., "Halogenation of Pyridinium-N-(2'-pyridyl)aminide. An Easy Synthesis of Halo-2-aminopyridines," Tetrahedron, vol. 51, pp. 8649–8654 (1995). Reaction of these compounds with the corresponding N-halosuccinimide in the reported conditions yielded the haloaminides 5f–i. See C. Burgos et al., 1995. The reaction between the aminides 5 and the quinones 6 was performed using silica as acid catalyst in acetonitrile. The process was accomplished at room temperature for 25–50 h.

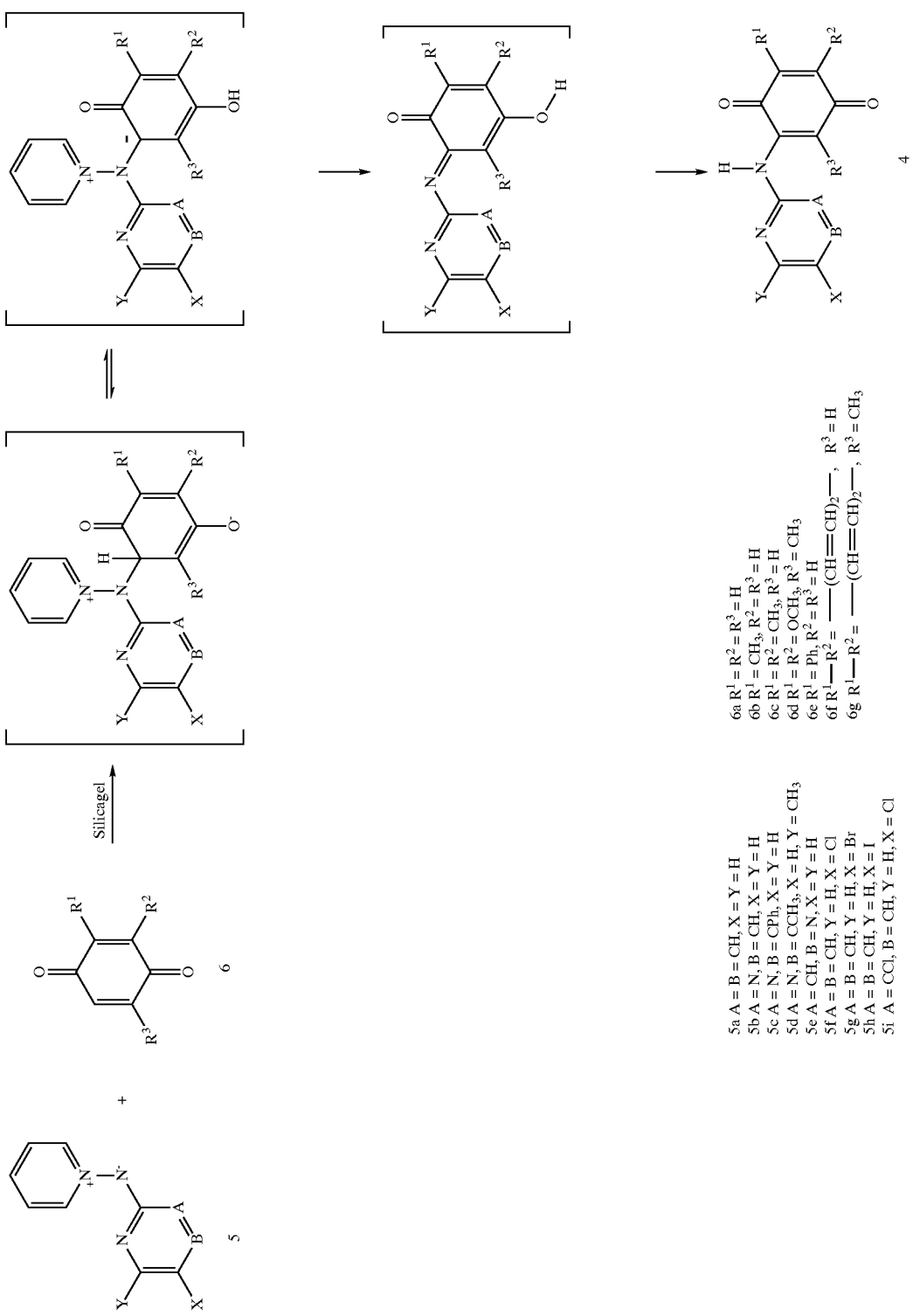

In compounds 4b, 4c and 4f (defined as in Table 1), heating the reaction mixture that was absorbed on silica under reduced pressure (~0.2 atm) at 30° C. improved the yields with a decrease in reaction times (5–10 min). The synthesis of 4n was only possible, even though in low yield, under microwave irradiation. As it can be seen in the proposed mechanism above, the aminide is acting as nucleophile toward the quinone through a Michael addition. The initially formed adduct eliminated pyridine and yielded the monosubstituted quinone. See T. Sasaki et al., "Nucleophilic Reactions of N-ethoxycabonyliminopyridinium Ylide with α,β-Unsaturated Carbonyl Compounds," Tetrahedron, vol. 28, pp. 1469–1476 (1972). When 2-methyl-1,4-benzoquinone 6b was used as starting material, a mixture of the two possible regioisomers was obtained in all cases (4b and 4c, 4o and 4p, 4v and 4x). On the contrary, compound 4f was the only regioisomer isolated in the reaction of 2-phenyl-1,4-benzoquinone 6e and N-(pyridin-2-yl)pyridinium aminide 5a, probably due to both the steric hindrance and the electronic effects produced by the phenyl substituent.

XXXIV. Syntheses of some Heterocyclic Hidrazine Compounds and their 9§ Action on Tubercle Bacilli," J. Pharm. Soc. Japan, vol. 73, pp. 598–601 (1953); P. J. Nelson et al., "1,2,4-Triazoles, VI. Synthesis of some s-Triazolo[4,3-a] pyrazines," J. Org. Chem., vol. 27, pp. 3243–3248 (1962); J. Chesterfield et al., "Pyrimidines. VIII. Halo- and Hidrazinopyrimidines," J. Chem. Soc., vol. 1955, pp. 3478–3481 (1955); and M. P. V. Boarland et al., "Pyrimidines. IV. Experiments on the Synthesis of Pyrimidine and 4,6-Dimethylpyrimidine," J. Chem. Soc., vol 1952, pp. 4691–4695 (1952). Pyridinium salts and aminides were obtained as reported. See R. Carceller et al., "Azinium-N-(2'-azinyl)aminides: Synthesis, Structure and Reactivity," Tetrahedron, vol. 50, pp. 4995–5012(1994); and C. Burgos et al., "Halogenation of Pyridinium-N-(2'-pyridyl)aminide. An Easy Synthesis of Halo-2-aminopyridines," Tetrahedron, vol 51, pp. 8649–8654 (1995).

Synthesis of Azin-2-ylaminoquinones

Generalprocedure A. Into a mixture of N-(azin-2-yl) pyridinium aminide (2.0 mmol), the corresponding α,β-

TABLE 1

Structures of quinones of general formula 4, designated Compounds 4b–4y, and Percent Inhibition of 5-lipoxygenase.

| Compound | A | B | X | Y | $R^1$ | $R^2$ | $R^3$ | % Inhibition[a] ($IC_{50}$)[b] |
|---|---|---|---|---|---|---|---|---|
| 4b | CH | CH | H | H | $CH_3$ | H | H | 86 ± 2.3 |
| 4c | CH | CH | H | H | H | $CH_3$ | H | 94 ± 2.7 (0.018 ± 0.004)[b] |
| 4d | CH | CH | H | H | $CH_3$ | $CH_3$ | H | 88 ± 5.2 |
| 4e | CH | CH | H | H | $OCH_3$ | $OCH_3$ | $CH_3$ | 92 ± 4.7 (0.155 ± 0.008) |
| 4f | CH | CH | H | H | Ph | H | H | 64 ± 4.3 |
| 4g | CH | CH | Cl | H | $OCH_3$ | $OCH_3$ | $CH_3$ | —[c] |
| 4h | CH | CH | Br | H | $OCH_3$ | $OCH_3$ | $CH_3$ | —[c] |
| 4i | CH | CH | H | H | —(CH=CH)$_2$— | | H | 100 ± 0.4 (0.045 ± 0.005) |
| 4j | CH | CH | H | H | —(CH=CH)$_2$— | | $CH_3$ | —[c] |
| 4k | CH | CH | Cl | H | —(CH=CH)$_2$— | | H | 24 ± 3.7 |
| 4l | CH | CH | Br | H | —(CH=CH)$_2$— | | H | 100 ± 0.5 (0.142 ± 0.009) |
| 4m | CH | CH | I | H | —(CH=CH)$_2$— | | H | —[c] |
| 4n | CCl | CH | Cl | H | —(CH=CH)$_2$— | | H | —[c] |
| 4o | N | CH | H | H | $CH_3$ | H | H | 56 ± 3.1 |
| 4p | N | CH | H | H | H | $CH_3$ | H | 62 ± 1.7 |
| 4q | N | CH | H | H | $OCH_3$ | $OCH_3$ | $CH_3$ | —[c] |
| 4r | N | CH | H | H | —(CH=CH)$_2$— | | H | 98 ± 1.1 (0.165 ± 0.007) |
| 4s | N | $CCH_3$ | H | $CH_3$ | $CH_3$ | $CH_3$ | H | 96 ± 1.7 (0.175 ± 0.011) |
| 4t | N | $CCH_3$ | H | $CH_3$ | —(CH=CH)$_2$— | | H | 98 ± 1.3 (0.161 ± 0.008) |
| 4u | N | CPh | H | H | —(CH=CH)$_2$— | | H | —[c] |
| 4v | CH | N | H | H | $CH_3$ | H | H | —[c] |
| 4x | CH | N | H | H | H | $CH_3$ | H | —[c] |
| 4y | CH | N | H | H | —(CH=CH)$_2$— | | H | —[d] |

[a]Data reported as percent inhibition of $LTB_4$ formation, at 1 μM, on rabbit peritoneal neutrophils (PMNL), as explained below in Example **. Data are indicated as the mean ± s.d. of three different experiments performed in duplicate.
[b]$IC_{50}$ data are reported in parentheses. $IC_{50}$ was calculated as the concentration of the test compound required to cause 50% inhibition of $LTB_4$ formation, measured on PMNL.
[c]No significant activity.
[d]180% activation at 0.1 μM.

General Chemical Methods

After synthesis, melting points of the new derivatives were recorded on an Electrothermal IA6304 and are reported uncorrected. $^1$H NMR spectra were obtained on a Varian Unity 300 spectrometer at 300 MHz. IR spectra were recorded on a Perkin Elmer 1310 spectrophotometer using KBr pellets. Mass spectra were determined on a Hewlett-Packard 5988A (70 eV). Flash chromatography was carried out using Merck Kieselgel 60 (230–400 mesh), which also was used to perform solid-supported reactions. Solvents and reagents were available commercially (e.g., Sigma-Aldrich, Inc.), and were purified by standard procedures. 2-Hydrazinoazines were prepared according to known procedures. See K. Shirakawa et al., "Chemotherapeutics unsaturated carbonyl derivative (2.0 mmol) and silica gel (2.0 g) in dry acetonitrile (10 mL) were stirred at room temperature for the period indicated below. The silica was removed by filtration, the solvent evaporated, and the residue was purified by flash chromatography and recrystallized if necessary.

General procedure B. N-(azin-2-yl)pyridinium aminide (2.0 mmol), the corresponding α,β-unsaturated carbonyl derivative (2.0 mmol) and silica gel (2.0 g) in dry acetonitrile (10 mL) were stirred, the solvent evaporated to dryness in vacuo (~0.2 atm) heating at 30° C., and the residue was purified by flash chromatography and recrystallized if necessary.

EXAMPLE 1

Synthesis of 2-(Pyridin-2-ylamino)-[1,4]benzoquinone (4a).

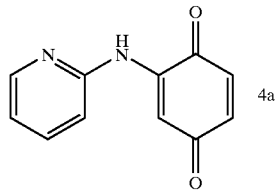

Following the general procedure A given above, N-(pyridin-2-yl)pyridinium aminide (0.1 g, 0.59 mmol) and [1,4]-benzoquinone (0.06 g, 0.59 mmol) were stirred for 26 h. This mixture yielded Compound 4a (0.07 g, 64%) after elution of the column with hexane/ethyl acetate (7:3 v/v) as a red solid: mp 102–104° C. (literature value, 102–103° C.; R. Carceller et al., 1994). IR (KBr)$n_{max}$ 3318, 1670, 1630, 1586, 1528, 1478 cm$^{-1}$. $^1$H NMR (DMSO-d$_6$) d 9.15: (brs, 1H, NH), 8.33 (dd, 1H, J=4.8, 2.0 Hz, H-6'), 7.76–7.66 (m, 2H, H-4',3), 7.48 (d, 1H, J=8.4 Hz, H-3'), 7.00 (dd, 1H, J=7.1, 4.7 Hz, H-5'), 6.84 (d, 1H, J=10.2 Hz, H-6), 6.72 (dd, 1H, J=10.2, 2.2 Hz, H-5) ppm. MS (EI) m/z 200 (M$^+$, 72); 172 (25); 144 (46); 118 (100); 78 (71); 51 (16).

Quantitative Analysis. Calculated for $C_{11}H_8N_2O_2$.

| $C_{11}H_8N_2O_2$ | % C | % H | % N |
|---|---|---|---|
| Calculated | 66 | 4.03 | 13.99 |
| Found | 66.05 | 3.85 | 13.89 |

EXAMPLE 2

Synthesis of 2-Methyl-6-(pyridin-2-ylamino)-[1,4]benzoquinone (4b) and 2-Methyl-5-(pyridin-2-ylamino)-[1,4]benzoquinone (4c).

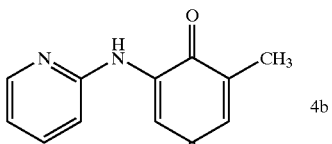

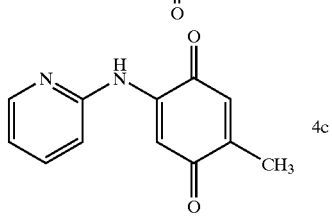

Following the general procedure B described above, N-(pyridin-2-yl)pyridinium aminide (0.86 g, 5.04 mmol) and methyl-[1,4]-benzoquinone (0.61 g, 5.04 mmol) were absorbed in silica gel. This resulted in a mixture of Compound 4b (0.36 g, 34%) and Compound 4c (0.42 g, 40%) which were separated by column chromatography on alumina after elution with hexane/ethyl acetate (7:3 v/v).

Compound 4b, 2-Methyl-6-(pyridin-2-ylamino)-[1,4] benzoquinone, was a red solid: mp 162–164° C. IR(KBr) $v_{max}$ 3320, 1644, 1588, 1520, 1478cm$^{-1}$. $^1$H NMR (DMSO-d$_6$) δ 9.13 (brs, 1H, NH), 8.32 (dd, 1H, J=5.1, 2.2 Hz, H-6'), 7.70 (ddd, 1H, J=9.1, 7.3, 2.0 Hz, H-4'), 7.62 (d, 1H, J=2.5 Hz, H-5), 7.47 (d, 1H, J=8.4 Hz, H-3'), 6.99 (dd, 1H, J=7.3, 5.1 Hz, H-5'), 6.58–6.56 (m, 1H, H-3), 2.00.(d, 3H, J=1.6 Hz, CH$_3$) ppm. MS (EI) m/z 214 (M$^+$, 76); 186 (19); 157 (50); 118 (100); 78 (74); 51 (15).

Quantitative Analysis. Calculated for $C_{12}H_{10}N_2O_2$.

| $C_{12}H_{10}N_2O_2$ | % C | % H | % N |
|---|---|---|---|
| Calculated | 67.28 | 4.7 | 13.08 |
| Found | 67.4 | 4.32 | 13.2 |

Compound 4c, 2-Methyl-5-(pyridin-2-ylamino)-[1,4] benzoquinone, was a red solid: mp 137–139° C. IR (KBr) $v_{max}$ 3308, 1673, 1646, 1590, 1531, 1484 cm$^{-1}$. $^1$H NMR (DMSO-d$_6$) δ 9.12 (brs, 1H, NH), 8.33 (dd, 1H, J=4.9, 2.0 Hz, H-6'), 7.70 (ddd, 1H, J=8.6, 7.1, 2.0 Hz, H-4'), 7.67 (s, 1H, H-6), 7.47 (d, 1H, J=8.0 Hz, H-3'), 7.00 (dd, 1H, J=7.1, 4.7 Hz, H-5'), 6.70 (q, 1H, J=1.5 Hz, H-3), 1.97 (d, 3H, J=1.6 Hz, CH$_3$) ppm. MS (EI) m/z 214 (M$^+$, 91); 186 (26); 158 (44); 118 (100); 78 (80); 51 (15).

Quantitative Analysis. Calculated for $C_{12}H_{10}N_2O_2$.

| $C_{12}H_{10}N_2O_2$ | % C | % H | % N |
|---|---|---|---|
| Calculated | 67.28 | 4.7 | 13.08 |
| Found | 67.5 | 4.38 | 12.79 |

EXAMPLE 3

Synthesis of 2,3-Dimethyl-5-(pyridin-2-ylamino)-[1,4]benzoquinone (4d)

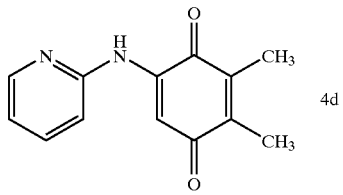

Compound 4d, 2,3-Dimethyl-5-(pyridin-2-ylamino)-[1,4] benzoquinone, was synthesized following the general procedure A as given above. N-(pyridin-2-yl)pyridinium aminide (2.46 g, 14.4 mmol).and 2,3-dimethyl-[1,4]-benzoquinone (1.97 g, 14.4 mmol) were stirred for 16 h. This gave a product (2.59 g, 79%) after elution with methylene chloride as a red solid: mp 177–178° C. IR(KBr) $v_{max}$ 3319, 1660, 1643, 1592, 1516, 1477cm$^{-1}$. $^1$H NMR (DMSO-d$_6$) δ 9.17 (brs, 1H, NH), 8.32 (dd, 1H, J=4.9, 2.0 Hz, H-6'), 7.70 (ddd, 1H, J=8.4, 7.1, 2.0 Hz, H-4'), 7.64 (s, 1H, H-6), 7.47 (d, 1H, J=8.4 Hz, H-3'), 6.98 (dd, 1H, J=7.1,4.9 Hz, H-5'), 1.97(brs, 3H, CH₃), 1.94 (brs, 3H, CH₃) ppm.

Quantitative Analysis. Calculated for $C_{13}H_{12}N_2O_2$.

| $C_{13}H_{12}N_2O_2$ | % C | % H | % N |
| --- | --- | --- | --- |
| Calculated | 68.41 | 5.3 | 12.27 |
| Found | 68.31 | 5.29 | 12.29 |

EXAMPLE 4

Synthesis of 2,3-Dimethoxy-5-methyl-6-(pyridin-2-ylamino)-[1,4]benzoquinone (4e)

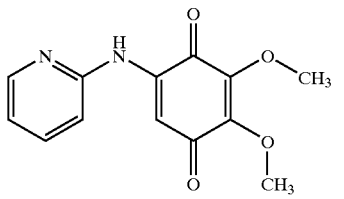

Synthesis of Compound 4e, 2,3-Dimethoxy-5-methyl-6-(pyridin-2-ylamino)-[1,4]benzoquinone, followed the general procedure A as given above. N-(pyridin-2-yl)pyridinium aminide (0.09 g, 0.54 mmol) and 2,3-dimethoxy-5-methyl-[1,4]-benzoquinone (0.1 g, 0.54 mmol) were stirred for 48 h. This gave a product (0.073 g, 50%) after elution with hexane/ethyl acetate (7:3 v/v) as a red solid: mp 79–81° C. IR (KBr) $v_{max}$ 3293, 1668, 1628, 1592, 1526, 1470 cm⁻¹. ¹H NMR (DMSO-d₆) δ 8.70 (brs, 1H, NH), 8.08 (dd, 1H, J=4.7, 1.8 Hz, H-6'), 7.59 (ddd, 1H, J=9.1, 6.6, 1.8 Hz, H-4'), 6.94 (d, 1H, J=8.4 Hz, H-3'), 6.81 (dd, 1H, J=6.5, 5.1 Hz, H-5'), 3.92 (s, 3H, OCH₃), 3.83 (s, 3H, OCH₃), 1.70 (s, 3H, CH₃) ppm. MS (EI) m/z 274 (M⁺, 12); 259 (100); 243 (7); 175 (24); 132 (23); 78 (51); 51 (10).

Quantitative Analysis. Calculated for $C_{14}H_{14}N_2O_4$

| $C_{14}H_{14}N_2O_4$ | % C | % H | % N |
| --- | --- | --- | --- |
| Calculated | 61.31 | 5.14 | 10.21 |
| Found | 61.37 | 5.1 | 10.22 |

EXAMPLE 5

Synthesis of 2-Phenyl-6-(pyridin-2-ylamino)-[1,4]benzoquinone (4f).

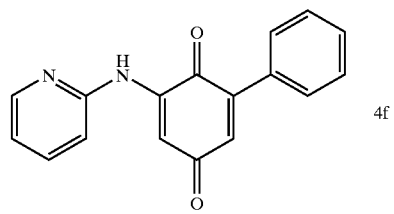

Synthesis of Compound 4f, 2-Phenyl-6-(pyridin-2-ylamino)-[1,4]benzoquinone, followed the general procedure B as given above. N-(pyridin-2-yl)pyridinium aminide (0.80 g, 4.67 mmol) and 2-phenyl-[1,4]-benzoquinone (0.86 g, 4.67 mmol) were absorbed in silica gel. This gave Compound 4f(1.15 g, 90%) after elution of the column with hexane/ethyl acetate (7:3 v/v) as a dark violet solid: mp 165–167° C. IR (KBr) $v_{max}$ 3328, 1672, 1628, 1584, 1520, 1476 cm⁻¹. ¹H NMR (DMSO-d₆) δ 9.25 (brs, 1H, NH), 8.36 (dd, 1H, J=4.8,2.2 Hz, H-6'), 7.76 (d, 1H, J=2.5 Hz, H-5), 7.73 (ddd, 1H, J=9.1, 7.3, 2.2 Hz, H-4'), 7.56–7.44 (m, 5H, Ph-H), 7.02 (dd, 1H, J=7.0, 5.1 Hz, H-5'), 6.76 (d, 1H, J=2.5 Hz, H-3) ppm. MS (EI) m/z 276 (M⁺, 15); 219 (25); 186 (100); 128 (24); 78 (16); 51 (6).

Quantitative Analysis. Calculated for $C_{17}H_{12}N_2O_2$.

| $C_{17}H_{12}N_2O_2$ | % C | % H | % N |
| --- | --- | --- | --- |
| Calculated | 73.9 | 4.38 | 10.14 |
| Found | 73.7 | 4.45 | 9.97 |

EXAMPLE 6

Synthesis of 2-(5-Chloropyridin-2-ylamino)-5,6-dimethoxy-3-methyl-[1,4]benzoquinone (4g)

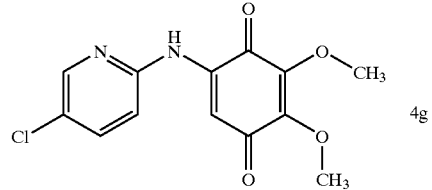

Synthesis of Compound 4g, 2-(5-Chloropyridin-2-ylamino)-5,6-dimethoxy-3-methyl-[1,4]benzoquinone, followed the general procedure A as described above. N-(5-chloropyridin-2-yl)pyridinium aminide (0.10 g, 0.49 mmol) and 2,3-dimethoxy-5-methyl-[1,4]-benzoquinone (0.089 g, 0.49 mmol) were stirred for 24 h. This gave the product, compound 4g (0.013 g, 9%), after elution with hexane/ethyl acetate (1:4v/v) as a violet solid: mp 106–108° C. IR (KBr) $v_{max}$ 3339, 1666, 1639, 1613, 1590, 1514, 1479 cm⁻¹. ¹H NMR (CDCl₃) δ 8.22 (d, 1H, J=2.6 Hz, H-6'), 7.56 (dd, 1H, J=8.8, 2.6 Hz, H-4'), 7.28 (brs, 1H, NH), 6.66 (d, 1H, J=8.8 Hz, H-3'), 4.09 (s, 3H, OCH₃), 1.74 (s, 3H, CH₃) ppm. Quantitative Analysis. Calculated for $C_{14}H_{13}ClN_2O_4$.

| $C_{14}H_{13}ClN_2O_4$ | % C | % H | % N |
| --- | --- | --- | --- |
| Calculated | 54.47 | 4.24 | 9.07 |
| Found | 54.5 | 3.94 | 8.91 |

EXAMPLE 7

Synthesis of 2-(5-Bromopyridin-2-ylamino)-5,6-dimethoxy-3-methyl-[1,4]benzoquinone (4h)

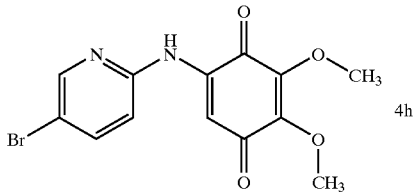

Synthesis of Compound 4h, 2-(5-Bromopyridin-2-ylamino)-5,6-dimethoxy-3-methyl-[1,4]benzoquinone, followed the general procedure A as described above. N-(5-bromopyridin-;2-yl)pyridinium aminide (0.10 g, 0.40 mmol) and 2,3-dimethoxy-5-methyl-[1,4]-benzoquinone (0.073 g, 0.40 mmol) were stirred for 48 h. This yielded Compound 4h (0.047 g, 33%) after elution with hexane/ethyl acetate (13 v/v) as a violet solid: mp 99–100° C. (EtOAc). IR (KBr) $v_{max}$ 3335, 1672, 1636, 1613, 1587, 1510, 1474 cm$^{-1}$. $^1$H NMR (CDCl$_3$) δ 8.31 (d, 1H, J=2.2 Hz, H-6'), 7.69 (dd, 1H, J=8.8, 2.2 Hz, H-4'), 7.26 (brs, 1H, NH), 6.61 (d, 1H, J=8.8 Hz, H-3'), 4.10 (s, 3H, OCH$_3$), 3.95 (s, 3H, OCH$_3$), 1.58 (s, 3H, CH$_3$) ppm.

Quantitative Analysis. Calculated for $C_{14}H_{13}BrN_2O_4$.

| $C_{14}H_{13}BrN_2O_4$ | % C | % H | % N |
| --- | --- | --- | --- |
| Calculated | 47.61 | 3.71 | 7.93 |
| Found | 47.78 | 3.52 | 7.87 |

EXAMPLE 8

Synthesis of 2-(Pyridin-2-ylamino)-[1,4]naphthoquinone (4i)

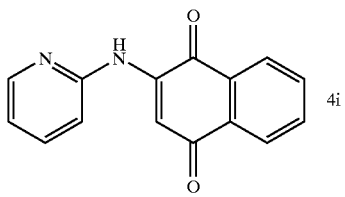

Synthesis of Compound 4i, 2-(Pyridin-2-ylamino)-[1,4]naphthoquinone, followed the general procedure A as described above. N-(pyridin-2-yl)pyridinium aminide (0.25 g, 1.46 mmol) and [1,4]-naphthoquinone (0.23 g, 1.46 mmol) were stirred for 24 h. This gave Compound 4i (0.34 g, 94%) after elution with hexane/ethyl acetate (7:3 v/v) as a red solid: mp 205–206° C. (reported value, 198–200° C.; See R. Carceller et al., 1994). IR (KBr) $v_{max}$ 3334, 1666, 1612, 1528, 1482 cm$^{-1}$. $^1$H NMR (DMSO-d$_6$) δ 9.45 (brs, 1H, NH), 8.40 (dd, 1H, J=5.1, 2.0 Hz, H-6'), 8.07 (dd, 1H, J=7.3, 1.6 Hz, H-5 or H-8), 8.03 (s, 1H, H-3), 7.96 (dd, 1H, J=7.5, 1.7 Hz, H-5 or H-8), 7.86 (ap.td, 1H, J=7.3, 1.6 Hz, H-6 or H-7), 7.80 (ap.td, 1H, J=7.3, 1.7 Hz, H-6 or H-7), 7.76 (ddd, 1H, J=8.1, 7.2, 2.0 Hz, H-4'), 7.57 (d, 1H, J=8.5 Hz, H-3'), 7.05 (4d, 1H, J=7.1,4.7 Hz, H-5') ppm. MS (EI) m/z 250 (M$^+$, 100); 221 (57); 194 (65); 78 (38); 51 (12).

Quantitative Analysis. Calculated for $C_{15}H_{12}N_2O_2$.

| $C_{15}H_{10}N_2O_2$ | % C | % H | % N |
| --- | --- | --- | --- |
| Calculated | 71.99 | 4.03 | 11.19 |
| Found | 71.78 | 3.94 | 10.87 |

EXAMPLE 9

Synthesis of 2-Methyl-3-(pyridin-2-ylamino)-[1,4]naphthoquinone (4j)

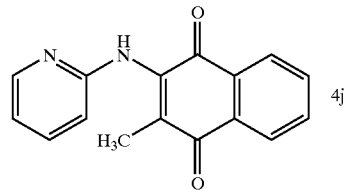

Synthesis of Compound 4j, $^2$-Methyl-3-(pyridin-2-ylamino)-[1,4]naphthoquinone, followed the general procedure A as described above. N-(pyridin-2-yl)pyridinium aminide (0.20 g, 1.16 mmol) and 2-methyl-[1,4]-naphthoquinone (0.20 g, 1.16 mmol) were stirred for 22 days. This yielded Compound 4j (0.20 g, 7%) after elution with hexane/ethyl acetate (7:3 v/v) as an orange solid: mp 130–132° C. IR (KBr) $v_{max}$ 3298, 1664, 1626, 1580, 1464 cm$^{-1}$. $^1$H NMR (DMSO-d$_6$) δ 8.90 (brs, 1H, NH), 8.10 (dd, 1H, J=4.8, 1.8 Hz, H-6'), 7.99 (dd, 1H, J=7.0, 1.5 Hz, H-5 or H-8), 7.95 (dd, 1H, J=7.1, 1.5 Hz, H-5 or H-8), 7.84–7.74 (m, 2H, H-6, 7), 7.63 (ap.td, 1H, J=7.7, 1.8 Hz, H-4'), 7.02 (d, 1H, J=8.5 Hz, H-3'), 6.85 (dd, 1H, J=6.9, 5.1 Hz, H-5'), 1.87 (s, 3H, CH$_3$) ppm. MS (EI) m/z 264 (M$^+$, 12); 249 (8); 169 (36); 105 (83); 78 (10); 51 (11).

Quantitative Analysis. Calculated for $C_{16}H_{12}N_2O_2$.

| $C_{16}H_{12}N_2O_2$ | % C | % H | % N |
| --- | --- | --- | --- |
| Calculated | 72.72 | 4.58 | 10.6 |
| Found | 72.85 | 4.46 | 10.83 |

EXAMPLE 10

Synthesis of 2-(5-Chloropyridin-2-ylamino)-[1,4]naphthoquinone (4k)

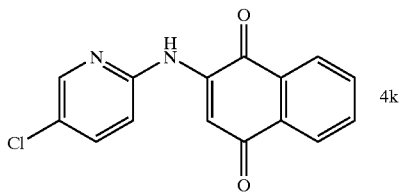

Synthesis of Compound 4k, 2-(5-Choropyridin-2-ylamino)-[1,4]naphthoquinone, followed the general procedure A as described above. N-(5-chloropyridin-2-yl) pyridinium aminide (0.10 g, 0.49 mmol) and [1,4]- naphthoquinone (0.078 g, 0.49 mmol) were stirred for 18 h. This yielded Compound 4k (0.114 g, 82%) after elution with ethyl acetate/hexane (1:4 v/v), as an orange solid: mp251–252° C.(EtOAc—CH$_2$Cl$_2$). IR(KBr) $v_{max}$ 3327, 1661, 1639, 1611, 1585, 1521, 1474 cm$^{-1}$. $^1$H NMR (CDCl$_3$) δ 8.35 (d, 1H, J=2.2 Hz, H-6'), 8.15–8.11 (m, 2H, H-5, 8), 8.06 (brs, 1H, NH), 7.93 (s, 1H, H-3), 7.78 (ap.td, 1H, J=7.3, 1.1 Hz, H-6 or H-7), 7.69 (ap.td, 1H, J=7.3, 1.1 Hz, H-6 or H-7), 7.62 (dd, 1H, J=8.8, 2.6 Hz, H-4'), 6.94 (d, 1H, J=8.8 Hz, H-3') ppm.

Quantitative Analysis. Calculated for C$_{15}$H$_9$ClN$_2$O$_2$.

| C$_{15}$H$_9$ClN$_2$O$_2$ | % C | % H | % N |
|---|---|---|---|
| Calculated | 63.28 | 3.19 | 9.84 |
| Found | 63.18 | 3.04 | 10 |

EXAMPLE 11

Synthesis of 2-(5-Bromopyridin-2-ylamino)-[1,4]naphthoquinone (4l)

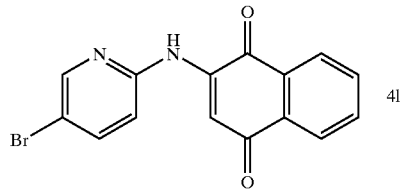

Synthesis of Compound 4l, 2-(5-Bromopyndin-2-ylamino)-[1,4]naphthoquinone, followed the general procedure A as described above. N-(5-bromopyridin-2-yl) pyridinium aminide (0.10 g, 0.4 mmol) and [1,4]-naphthoquinone (0.063 g, 0.4 mmol) were stirred for 18 h. This yielded Compound 4l (0.13 g, 96%) after elution with hexane/ethyl acetate (4:1 v/v) as a red solid: mp 243–244° C. (EtOAc—CH$_2$Cl$_2$). IR (KBr) $v_{max}$ 3302, 1663, 1635, 1612, 1583, 1512, 1469 cm$^{-1}$. $^1$H NMR (CDCl$_3$) δ 8.44 (d, 1H, J=2.6 Hz, H-6'), 8.13–8.10 (m, 2H, H-5, 8), 8.06 (brs, 1H, NH), 7.93 (s,1H, H-3), 7.77 (ap.td, 1H, J=7.3, 1.1 Hz, H-6 or H-7), 7.75 (dd, 1H, J=8.6, 2.6 Hz, H-4'), 7.69 (ap.td, 1H, J=7.3, 1.1 Hz, H-6 or H-7), 7.35 (d, 1H, J=8.6 Hz, H-3') ppm.

Quantitative Analysis. Calculated for C$_{15}$H$_9$BrN$_2$O$_2$.

| C$_{15}$H$_9$BrN$_2$O$_2$ | % C | % H | % N |
|---|---|---|---|
| Calculated | 54.74 | 2.76 | 8.51 |
| Found | 54.8 | 2.94 | 8.77 |

EXAMPLE 12

Synthesis of 2-(5-Iodpyridin-2-ylamino)-[1,4]naphthoquinone (4m)

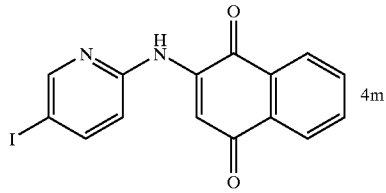

Synthesis of Compound 4m, 2-(5-Iodopyridin-2-ylamino)-[1,4]naphthoquinone, followed the general procedure A as described above. N-(5-iodopyridin-2-yl) pyridinium aminide (0.28 g, 1.0 mmol) and [1,4]-naphthoquinone (0.16 g, 1.0 mmol) were stirred for 18 h. This yielded Compound 4m (0.12 g, 34%) after elution with hexane/ethyl acetate (1:4 v/v) as an orange solid: mp 245–246° C. (EtOAc—CH$_2$Cl$_2$). IR (KBr) $v_{max}$ 3235; 1675, 1629, 1607, 1567, 1504, 1466 cm$^{-1}$. $^1$H NMR (CDCl$_3$) δ 8.58 (d, 1H, J=2.6 Hz, H-6'), 8.14–8.11 (m, 2H, H-5, 8), 8.04 (brs, 1H, NH), 7.92 (s, 1H, H-3), 7.90 (dd, 1H, J=8.8, 2.2 Hz, H-4'), 7.78 (ap.t, 1H, J=7.3, 1.5 Hz, H-6 or H-7), 7.69 (ap.td, 1H, J=7.3, 1.5 Hz, H-6 or H-7), 6.81 (d, 1H, J=8.8 Hz, H-3') ppm.

Quantitative Analysis. Calculated for C$_{15}$H$_9$IN$_2$O$_2$.

| C$_{15}$H$_9$IN$_2$O$_2$ | % C | % H | % N |
|---|---|---|---|
| Calculated | 47.9 | 2.41 | 7.45 |
| Found | 47.78 | 2.54 | 7.87 |

EXAMPLE 13

Synthesis of 2-(3,5-Dichloropyridin-2-ylamino)-[1,4]naphthoquinone (4n).

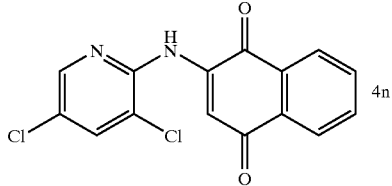

Synthesis of Compound 4n, 2-(3,5-Dichloropyridin-2-ylamino)-[1,4]naphthoquinone (4n) was by the following procedure: A mixture of N-(3,5-dichloropyridin-2-yl) pyridinium aminide (0.65 g, 2.71 mmol) and [1,4]-naphthoquinone (0.43 g, 2.71 mmol) was absorbed on silica gel, and then irradiated under a microwave at a.: power output of 400 watts for 8 min. A commercial microwave oven with 900 watts of power output was used. The power generated by the oven was measured before every experiment by the method described by R. W. Watkins, "Heating in Microwave Ovens. An Example of Dipole Moment in Action," J. Chem. De., vol. 60, pp. 1043 (1983). This yielded Compound 4n (0.04 g, 5%) after elution with hexane/ethyl acetate (4:1 v/v) as an orange solid: mp 249–250° C. (EtOAc—CH$_2$Cl$_2$). IR (KBr) $v_{max}$ 3311, 1666, 1642, 1621, 1585, 1514, 1459 cm$^{-1}$. $^1$H NMR (DMSO-d$_6$) δ 8.76 (brs, 1H; NH), 8.51 (d, 1H, J=2.4 Hz, H-6'), 8.30 (d, 1H, J=2.2 Hz, H-4'), 8.09 (dd, 1H, J=7.3, 1.6 Hz, H-5 or H-8), 7.99 (dd, 1H, J=7.31, 1.6 Hz, H-5 or H-8), 7.90 (td, 1H, J=7.3, 1.6 Hz, H-6 or H-7), 7.84 (td, 1H, J=7.3, 1.6 Hz, H-6 or H-7), 7.80 (s, 1H, H-3) ppm.

Quantitative Analysis. Calculated for $C_{15}H_8Cl_2N_2O_2$.

| $C_{15}H_8Cl_2N_2O_2$ | % C | % H | % N |
|---|---|---|---|
| Calculated | 56.45 | 2.53 | 8.78 |
| Found | 56.66 | 2.59 | 8.87 |

EXAMPLE 14

Synthesis of 2-Methyl-6-(pyrimidin-2-ylamino)-[1,4]benzoquinone (4o) and 2-Methyl-5-(pyrimidin-2-ylamino)-[1,4]benzoquinone (4p).

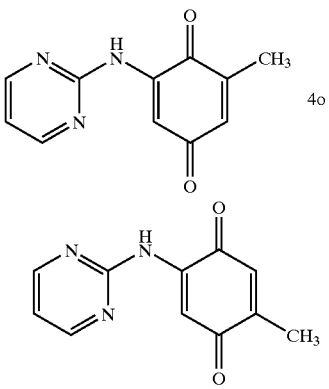

Synthesis of Compound 4o, 2-Methyl-6-(pyrimidin-2-ylamino)-[1 4]benzoquinone, and Compound 4p, 2-Methyl-5-(pyrimidin-2-ylamino)-[1,4]benzoquinone, followed the general procedure A as given above. N-(pyrimidin-2-yl) pyridinium aminide (0.1 g, 0.58 mmol) and methyl-[1,4]-benzoquinone (0.07 g, 0.58 mmol) were stirred for 16 h. This yielded a mixture of Compound 4o (0.040 g, 34%) and Compound 4p (0.066 g, 55%), which were separated by column chromatography on alumina after elution with hexane/ethyl acetate (7:3 v/v).

Compound 4o was an orange solid: mp 167–169° C. (hexane-EtOAc); IR (KBr) $v_{max}$ 3228, 1654, 1605, 1575, 1522, 1442 cm$^{-1}$; $^1$H NMR (DMSO-d$_6$) δ 8.68 (d, 2H, J=4.8 Hz, H-4',6'), 8.45 (brs, 1H, NH), 7.46–7.45 (m, 1H, H-5), 7.14 (t, 1H, J=4.8 Hz, H-5'), 6.66–6.62 (m, 1H, H-3), 2.01 (d, 3H, J=1.1 Hz, CH$_3$) ppm.

Quantitative Analysis. Calculated for $C_{11}H_9N_3O_2$.

| $C_{11}H_9N_3O_2$ | % C | % H | % N |
|---|---|---|---|
| Calculated | 61.39 | 4.21 | 19.52 |
| Found | 61.44 | 4.38 | 19.21 |

Compound 4p was an orange solid: mp 172–174° C. (hexane-EtOAc); IR (KBr) $v_{max}$ 3552, 1669, 1647, 1609, 1587, 1531, 1450 cm$^{-1}$; $^1$H NMR (DMSO-d$_6$) δ 8.68 (d, 2H, J=5.1 Hz, H-4',6'), 8.39 (brs, 1H, NH), 7.50 (s, 1H, H-6), 7.14 (t, 1H, J=5.1 Hz, H-5'), 6.81–6.79 (m, 1H, H-3), 1.97 (d, 3H, J=1.1 Hz, CH$_3$) ppm.

Quantitative Analysis. Calculated for $C_{11}H_9N_3O_2$.

| $C_{11}H_9N_3O_2$ | % C | % H | % N |
|---|---|---|---|
| Calculated | 61.39 | 4.21 | 19.52 |
| Found | 61.03 | 4.44 | 19.23 |

EXAMPLE 15

Synthesis of 2,3-Dimethoxy-5-methyl-6-(pyrimidin-2-ylamino)-[1,4]benzoquinone (4q).

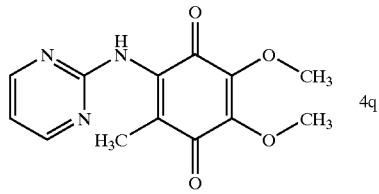

Synthesis of Compound 4q, 2,3-Dimethoxy-5-methyl-6-(pyrimidin-2-ylamino)-[1.4]benzoquinone, followed the general procedure A as described above. N-(pyrimidin-2-yl) pyridinium aminide (0.1 g, 0.58 mmol) and 2,3-dimethoxy-5-methyl-[1,4]-benzoquinone (0.105 g 0.58 mmol) were stirred for 24 h. This yielded C compound 4q (0.01 g, 6%) after elution with hexane/ethyl acetate (7:3 v/v) as a red solid: mp 132–134° C. (hexane-EtOAc); IR (KBr) $v_{max}$ 3208, 1655, 1615, 1570, 1522, 1417 cm$^{-1}$; $^1$H NMR (DMSO-d$_6$) δ 9.24 (brs, 1H, NH), 8.37 (d, 2H, J=5.1 Hz, H-4',6'), 6.82 (t, 1H, J=4.8 Hz, H-5'), 3.89 (s, 3H, OCH$_3$), 3.84 (s, 3H, OCH$_3$), 1.83 (s, 3H, CH$_3$) ppm.

Quantitative Analysis. Calculated for $C_{13}H_{13}N_3O_4$.

| $C_{13}H_{13}N_3O_4$ | % C | % H | % N |
|---|---|---|---|
| Calculated | 56.72 | 4.76 | 15.26 |
| Found | 56.91 | 4.5 | 15.17 |

EXAMPLE 16

Synthesis of 2-(Pyrimidin-2-ylamino)-[1,4]naphthoquinone (4r)

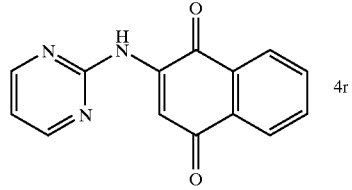

Synthesis of Compound 4r, 2-(Pyrimidin-2-ylamino)-[1,4]naphthoquinone, followed the general procedure A as described above. N-(pyrimidin-2-yl)pyridinium aminide (0.1 g, 0.58 mmol) and [1,4]-naphthoquinone (0.091 g, 0.58 mmol) were stirred for 6 h. This yielded Compound 4r (0.07 g, 70%) after elution with hexane/ethyl acetate (7:3 v/v) as a yellow solid: mp 245–247° C. (hexane-EtOAc); IR (KBr) $v_{max}$ 3229, 1675, 1644, 1575, 1517, 1437 cm$^{-1}$; $^1$H NMR (DMSO-d$_6$) δ 8.73 (d, 2H, J=4.8 Hz, H-4',6'), 8.69 (brs, 1H, NH), 8.07 (dd, 1H, J=7.31, 1.8 Hz, H-5 or H-8), 7.98 (dd, 1H, J=7.2, 1.8 Hz, H-5 or H-8), 7.88 (ap.td, 1H, J=6.7, 1.8 Hz, H-6 or H-7), 7.84 (s, 1H, H-3), 7.82 (ap.td, 1H, J=6.6, 1.8 Hz, H-6 or H-7), 7.19 (t, 1H, J=4.8 Hz, H-5'), ppm.

Quantitative Analysis. Calculated for C$_{14}$H$_9$N$_3$O$_2$.

| C$_{14}$H$_9$N$_3$O$_2$ | % C | % H | % N |
|---|---|---|---|
| Calculated | 66.93 | 3.61 | 16.72 |
| Found | 66.75 | 3.88 | 16.31 |

EXAMPLE 17

Synthesis of 2,3-Dimethyl-5-(4,6-dimethylpyrimidin-2-ylamino)-[1,4]benzoquinone (4s)

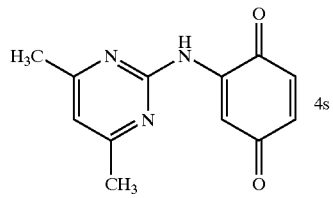

Synthesis of Compound 4s, 2,3-Dirnethyl-5-(4,6-dimethylpyfimidin-2-ylamino)-[1,4]benzoquinone, followed the general procedure A as described above. N-(4,6-dimethylpyrimidin 2-yl)pyridinium aminide (0.50 g, 2.5 mmol) and 2,3-dimethyl-[1,4]-benzoquinone (0.34 g, 2.5 prepared as described in J. M. Bruce et al., "Benzoquinones and Related Compounds. Part 3. Preparation of 1,4-Benzoquinones by Oxidation of Hydroquiniones with Manganese Dioxide," J. Chem. Research (S), vol. 1981, pp. 252–253 (1981); and L. I. Smith et al., "Quinones and Metallic Enolates XVI. Dibromo-o-xyloquinone and Sodium Malonic Ester," J. Am. Chem. Soc., vol. 64, pp. 528–533 (1942) were stirred for 18 h. This yielded Compound 4s (0.45 g, 70%) after elution with dichloromethane as an orange solid: mp 188–189° C.(EtOAc). IR (KBr)υ$_{max}$, 3368, 1645, 1610, 1525, 1449 cm$^{-1}$; $^1$H NMR (CDCl$_3$) δ 8.17 (brs, 1H, NE), 7.70 (s, 1H, H-6), 6.91 (s, 1H, H-5'), 2.06 (s, 6H, CH$_3$), 1.61 (s, 6H, CH$_3$) ppm.

Quantitative Analysis. Calculated for C$_{14}$H$_{15}$N$_3$O$_2$.

| C$_{14}$H$_{15}$N$_3$O$_2$ | % C | % H | % N |
|---|---|---|---|
| Calculated | 65.36 | 5.88 | 16.33 |
| Found | 65.35 | 5.83 | 6.44 |

EXAMPLE 18

Synthesis of 2-(4,6-Dimethylpyrimidin-2-ylamino)-[1,4]naphthoquinone (4t).

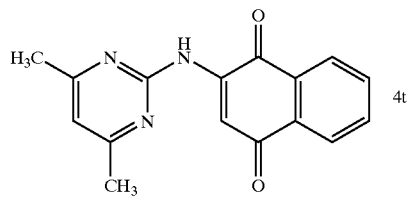

Synthesis of Compound 4t, 2-(4,6-Dimethylpyrimidin-2-ylamino)-[1,4]naphthoquinone, followed the general procedure A as described above. N-(4,6-dimethylpyrimidin-2-yl) pyridinium aminide (0.50 g, 2.5 mmol) and [1,4]-naphthoquinone (0.40 g, 2.5 mmol) were stirred for 18 h. This yielded Compound 4t (0.5.3 g, 76%) after elution with dichloromethane as a yellow solid: mp 196–197° C. (EtOAc); IR (KBr) v$_{max}$ 3335, 1673, 1638, 1617, 1590, 1536, 1444 cm$^{-1}$; $^1$H NMR (CDCl$_3$) δ 8.41 (brs, 1H, NH), 8.12–8.10 (m, 2H, H-5, 8), 8.07 (s, 1H, H-3), 7.74 (ap.t, 1H, J=7.3 Hz, H-6 or H-7), 7.67 (ap.t, 1H, J=7.3 Hz, H-6 or H-7), 6.67 (s, 1H, H-5'), 2.44 (s, 6H, CH$_3$) ppm.

Quantitative Analysis. Calculated for C$_{16}$H$_{13}$N$_3$O$_2$.

| C$_{16}$H$_{13}$N$_3$O$_2$ | % C | % H | % N |
|---|---|---|---|
| Calculated | 68.81 | 4.69 | 15.04 |
| Found | 68.99 | 4.68 | 14.98 |

EXAMPLE 19

Synthesis of 2-(4-Phenylpyrimidin-2-ylamino)-[1,4]naphthoquiniione (4u)

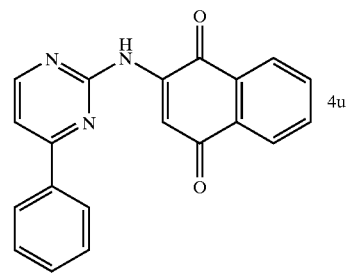

Synthesis of Compound 4u, 2-(4-Phenylpyrimidin-2-ylamino)-[1,4]naphthoquinone, followed the general procedure A as described above. N-(4-phenylpyrimidin-2-yl) pyridinium aminide (0.60 g, 2.42 mmol) and [1,4]-naphthoquinone (0.38 g, 2.42 mmol) were stirred for 18 h. This yielded Compound 4u (0.32 g, 40%) after elution with dichloromethane as a yellow solid: mp 229–230° C. (EtOAc); IR(kBr) v$_{max}$ 3356, 1667, 1640, 1619, 1581, 1531, 1498, 1450cm$^{-1}$; $^1$H NMR (DMSO-d$_6$) δ 8.79 (brs, 1H, NH), 8.81 (d, 1H,. J=5.3 Hz, H-6'), 8.24–8.21 (m, 2H, H-3",5"), 8.11 (dd, 1H, J=7.3, 1.8 Hz, H-5 or H-8), 8.01 (dd, 1H, J=7.3, 1.8 Hz, H-5 or H-8), 7.94 (s, 1H, H-3), 7.90 (td, 1H, J=7.3, 1.8 Hz, H-6 or H-7), 7.85 (td, 1H, J=7.3, 1.8 Hz, H-6 or H-7), 7.78 (d, 1H, J=5.3 Hz, H-5'), 7.61–7.59 (m, 3H, H-2",4",6") ppm.

Quantitative Analysis. Calculated for $C_{20}H_{13}N_3O_2$.

| $C_{20}H_{13}N_3O_2$ | % C | % H | % N |
|---|---|---|---|
| Calculated | 73.38 | 4 | 12.84 |
| Found | 73.28 | 3.91 | 13.08 |

EXAMPLE 20

Synthesis of 2-Methyl-6-(pyrazin-2-ylamino)-[1,4]benzoquinone (4v) and 2-Methyl-5-(pyrazin-2-ylamino)-[1,4]benzoquinone (4x).

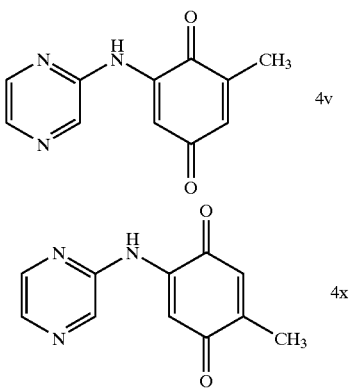

Synthesis of Compound 4v, 2-Methyl-6-(pyrazin-2-ylamino)-[1,4]benzoquinone, and Compound 4x, 2-Methyl-5-(pyrazin-2-ylamino)-[1,4]benzoquinone, followed the general procedure A as described above. N-(pyrazin-2-yl)pyridinium aminide[7b] (0.1 g, 0.58 mmol) and methyl-[1,4]-benzoquinone (0.07 g, 0.58 mmol) were stirred for 6 h. This yielded a mixture of Compound 4v (0.02 g, 17%) and Compound 4x (0.03 g, 25%), which were separated by column chromatography on alumina after elution with hexanelethyl acetate (7:3 v/v).

Compound, 4v was a orange solid: mp 168–170° C. (hexane-EtOAc); IR (KBr) $v_{max}$ 3323, 1641, 1583, 1508, 1395 cm$^{-1}$; $^1$H NMR (DMSO-d$_6$) δ 9.62 (brs, 1H, NH), 8.83 (d, 1H, J=1.5 Hz, H-3'), 8.33 (dd, 1H, J=2.9, 1.5 Hz, H-6'), 8.17 (d, 1H, J=2.7 Hz, H-5'), 7.56 (d, 1H, J=2.6 Hz, H-5), 6.62–6.60 (m, 1H, H-3), 2.00 (d, 3H, J=1.7 Hz, CH$_3$) ppm.

Quantitative Analysis. Calculated for $C_{11}H_9N_3O_2$.

| $C_{11}H_9N_3O_2$ | % C | % H | % N |
|---|---|---|---|
| Calculated | 61.39 | 4.21 | 19.52 |
| Found | 61.54 | 4.48 | 19.4 |

Compound 4x was an orange solid: mp 134–136° C. (hexane-EtOAc); IR (KBr) $v_{max}$ 3305, 1638, 1599, 1549, 1516, 1400 cm$^{-1}$; $^1$H NMR (DMSO-d$_6$) δ 9.59 (brs, 1H, NH), 8.82 (d, 1H, J=1.1 Hz, H-3'), 8.34 (dd, 1H, J=2.6, 1.4 Hz, H-6'), 8.17 (d, 1H, J=2.6 Hz, H-5'), 7.60 (s, 1H, H-6), 6.76–6.74 (m, 1H, H-3), 1.96 (d, 3H, J=1.5 Hz, CH$_3$) ppm.

Quantitative Analysis. Calculated for $C_{11}H_9N_3O_2$.

| $C_{11}H_9N_3O_2$ | % C | % H | % N |
|---|---|---|---|
| Calculated | 61.39 | 4.21 | 19.52 |
| Found | 61.37 | 4.34 | 19.6 |

EXAMPLE 21

Synthesis of 2-(Pyrazin-2-ylamino)-[1,4]naphthoquinone (4y)

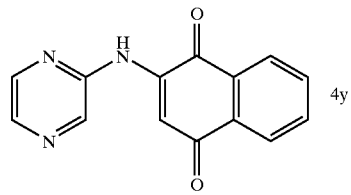

Synthesis of Compound 4y, 2-(Pyrazin-2-ylamino)-[i,4]naphthoquinone, followed the general procedure A as described above. N-(pyrazin-2-yl)pyridinium aminide (0.1 g, 0.58 mmol) and [1,4]-naphthoquinone (0.091 g, 0.58 mmol) were stirred for 24 h. This yielded Compound 4y (0.08 g, 56%) after elution with hexane/ethyl acetate (7:3 v/v) as a yellow solid: mp 245–247° C. (hexane-EtOAc); IR (KBr) $v_{max}$ 3333, 1659, 1640, 1613, 1585 cm$^{-1}$; $^1$H NMR (DMSO-d$_6$) δ 9.84 (bras, 1H, NH), 8.90(d, 1H, J=1.4 Hz, H-3'), 8.40 (dd, 1H, J=2.6, 1.4 Hz, H-6'), 8.23 (d, 1H, J=2.9 Hz, H-5'), 8.08 (4d, 1H, J=8.1, 1.4 Hz, H-5 or H-8), 7.96 (dd, 1H, J=7.3, 1.4 Hz, H-5 or H-8), 7.94 (s, 1H, H-3), 7.87 (ap.t, 1H, J=7.8, 1.5 Hz, H-6 or H-7), 7.82 (ap.t, 1H, J=8.4, 1.8 Hz, H-6 or H-7) pm.

Quantitative Analysis. Calculated for $C_{14}H_9N_3O_2$.

| $C_{11}H_9N_3O_2$ | % C | % H | % N |
|---|---|---|---|
| Calculated | 66.93 | 3.61 | 16.72 |
| Found | 67.15 | 3.87 | 16.51 |

EXAMPLE 22

Inhibition of 5-Lipoxygenase by (2-azinylamino)quinone Derivatives

The 5-LO enzyme, which is found primarily in cells of myeloid origin such as polymorphonuclear leukocytes ("PMNL"), eosinophils, and macrophages, catalyzes the first step of the biochemical pathway in which arachadonic acid ("AA") is,converted into LTA$_4$. Few cells actually possess the 5-LO enzyme, whereas virtually all cells possess LTA$_4$-hydrolase, which transforms LTA$_4$ into all other classes of LTs. To test the inhibition of the quinone derivatives on the activity of 5-LO rabbit polymorphonuclear leukocytes (PMNLs) were used.

Preparation of Rabbit Peritoneal PMNLs and Radiostopic Assay of 5-LO Activity Polymorphonuclear leukocytes (PMNLs) were purified from rabbits by glycogen-intraperitoneal elicited intraperitoneal recruitment, as descrited in T. Yatabe et al., "Studies on 5-lipoxygenase inhibitors: I. Synthesis and 5-lipoxygenase inhibitory activity of novel hydroxanic acid derivatives," chem. Pharm. Bull., vol. 46, pp. 966–972 (1998). An intraperitoneal injection of 300 mL of 0.1% (w/v) glycogen in sterile saline was administered 6 h before the rabbits were sacrificed by an intravascular injection of Nembutal. Peritoneal exudates were collected in 5 $\mu$M EGTA, and residual red cells were removed by lysis in ammonium chloride. These cell preparations were obtained with greater than 96% purity, as assessed by Wright-Giemsa staining and greater than 95% viability as assessed by Trypan blue exclusion.

PMNL cells in suspension were pre-incubated for 20 min at room temperature with $^{14}$C-labeled arachadonic acid (AA) and diluted to 3000 cells $\mu L^{-1}$. Thereafter, the calcium ionophore A-23187 (1 $\mu$g/mL) was added to stimulate $LTB_4$ production, and the cells further incubated for 15 min under stirring at 37° C. After incubation, the aqueous samples were successively shaken with a mixture of chloroform/methanol/formic acid (12:12:1) for 30 sec and then with chloroform for 10 sec. Organic phases containing $LTB_4$, 5-HPETE (5-hydroperoxyeicosatetraenoic acid), diHPETEs (dihydroperoxyeicosatetraenoic acids), and prostaglandins (PGs) were pooled, evaporated to dryness under nitrogen and dissolved into a small amount of chloroform-MeOH (1:1). Separation of the 5-LO metabolites was performed by thin layer chromatography (TLC) on silica gel G plates developed in diethyl ether-hexane-acetic acid (60:40:1, v/v/v).

Bands containing 5-lipoxygenase (5-LO) metabolites were scraped from the TLC plates, and $^{14}$C levels were quantitatively measured by liquid scintillation. 5-LO activity was an obtained from the amount of $^{14}$C-arachidonic acid converted into $LTB_4$ after the prelabeled PMNL cells were stimulated to produce LTB4 by the calcium ionophore as described above. $IC_{50}$ was calculated as the concentration of the 5-LO antagonist that produced 50% inhibition of the metabolite conversion.

The in vitro activity of the (2-azinylamino)quinone derivatives products as inhibitors of 5-lipoxygenase (5-LO) was determined on rat peritoneal PMNLs and expressed as a percent inhibition at 1 $\mu$M (Table 1). $IC_{50}$ values, calculated as theconcentration of test compound required to cause 50% inhibition of $LTB_4$ formation, were also determined for some representative examples. Compounds 4c, 4e, 4i, 4l, 4r, 4s and 4t were revealed as potent in vitro 5-LO inhibitors. These compounds, in general, correspond to compounds bearing the more lipophilic quinone fragments. Quinone 4c displayed the lowest $IC_{50}$ (18 nM), a value several times lower than that previously reported for the quinone form 3 as shown above. See S. Ohkawa et al., "Dual Inhibition of Thromboxane $A_2$ Synthetase and 5-Lipoxygenase with Scavenging Activity of Active Oxygen Species. Synthesis of a Novel Series of (3-Pyridylmethyl)benzoquinone Derivatives," J. Med. Chem., vol. 34, pp. 267–276 (1991).

In relation to the heterocyclic moiety, an interchange between a pyridine and a pyrimidine ring did not significantly increase the activity, as can be seen when comparing compounds 4c and 4i with 4p and 4r. Three compounds were obtained having a pyrazinyl moiety, 4v, 4x, and 4y. Only one, 4y, displayed agonist activity, the other two being inactive. In addition, halogen substitution of the pyridine moiety, as in 4k and 4l, showed significant inhibition of 5-LO only in the chloro-derivative, 4k.

A similar profile of 5-LO inhibition by quinones of the general formula 4 was obtained when the compounds were tested by radioimmunoassay ("RIA") in rat peritoneal PMNL. The results are presented in Table 2. Moreover, the quinone derivatives 4 were poor in vitro inhibitors of COX-1 and COX-2 activity when tested at a concentration 500 times higher than that used in the 5-LO assay (Table 2). The derivatives did not have any effect when tested at a concentration of 1 $\mu$M (datanot shown).

General Formula Quinone Derivatives 4

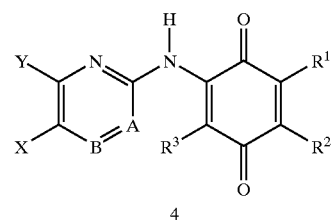

4

TABLE 2

Inhibitory effect of quinones 4
in 5-LO, COX-1 and COX-2 activity.

|  | COX-1 | COX-2 | 5-LO |
| --- | --- | --- | --- |
| Aspirin | 83.1 ± 2.0 | nt | nt |
| Indometacin | nt | 86.4 ± 1.2 | nt |
| Piroxicam | nt | 87.2 ± 3.8 | nt |
| NDGA | nt | nt | 92.0 ± 4.2 |
| 4c | 5.2 ± 6.2 | 20.1 ± 0.7 | 85.8 ± 13.1 |
| 4e | 11.2 ± 2.7 | 9.4 ± 0.4 | 95.4 ± 4.0 |
| 4i | 23.1 ± 4.6 | 16.5 ± 6.1 | 86.2 ± 10.0 |
| 4l | 16.8 ± 1.4 | 8.0 ± 3.6 | 85.5 ± 4.5 |
| 4p | 8.4 ± 6.4 | 0.0 ± 9.5 | 90.4 ± 3.3 |
| 4r | 14.4 ± 1.3 | 6.6 ± 14.9 | 96.4 ± 1.9 |
| 4s | 8.4 ± 11.6 | 3.3 ± 12.9 | 89.6 ± 2.3 |
| 4t | 8.2 ± 2.5 | 0.0 ± 15.1 | 86.3 ± 3.0 | nt = non-tested

The inhibitory effect of aspirin (for COX-1), indometacin and piroxicam (for COX-2) and quinones 4 on COX-1 and COX-2 activity was done at final concentration 500 $\mu$M. The 5-LO assay was done in the presence of inhibitors at AM final concentration including the selective 5-LO inhibitor NDGA. Percent inhibition mean values ±SD from at least three individual determinations are shown.

In vivo inhibitory effects over 5-LO on AAE test (as described in J. M. Young et al., "The Mouse Ear Inflammatory Response to Topical Arachidonic Acid," J. Invest. Dermatol., vol. 82, pp. 367–371 (1984); and E. E. Opas et al., "Prostaglandin and leukotriene Synthesis in Mouse Ears Inflammed by Arachidonic Acid," J. Invest. Dermatol., vol. 84, pp. 253–256 (1985)) were determined for the more active in vitro compounds (Table 3). The quinone 4c, which displayed the lowest $IC_{50}$ (Table 1) was the more active product. When 4c [100 mg (ear)] was co-applied with Indomethacin (as a COX-inhibitor), an additive effect was observed (from 66% inhibition to 89%). This result further supports the selectivity of 4c as an 5-LO inhibitor, as observed in the in vitro assay. Comparison of the products with standard antiinflarnatory compounds showed a good profile for several compounds.

General Formula Quinone Derivatives 4

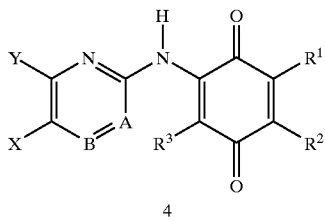

4

4. The compound of claim 1 which is 2,3-Dimethoxy-5-methyl-6-(pyridin-2-ylamino)-[1,4]benzoquinone (4e), or a pharmaceutically acceptable salt thereof.

5. The compound of claim 1 which is 2-Phenyl-6-(pyridin-2-ylamino)-[1,4]benzoquinone (4f), or a pharmaceutically acceptable salt thereof.

6. The compound of claim 1 which is 2-(5-Chloropyridin-2-ylamino)-5,6-dimethoxy-3-methyl-[1,4]benzoquinone (4g), or a pharmaceutically acceptable salt thereof.

7. The compound of claim 1 which is 2-(5-Bromopyridin-2-ylamino)-5,6-dimethoxy-3-methyl-[1,4]benzoquinone (4h), or a pharmaceutically acceptable salt thereof.

8. The compound of claim 1 which is 2-Methyl-6-(pyrimidin-2-ylamino)-[1,4]benzoquinone (4o), or a pharmaceutically acceptable salt thereof.

TABLE 3

Inhibitory effects of selected quinones 4 on the arachidonic acid-induced ear inflammation in mice.

| Comp. | A | B | X | Y | $R^1$ | $R^2$ | $R^3$ | % inhibition[a] | | |
|---|---|---|---|---|---|---|---|---|---|---|
| | | | | | | | | 250 µg/ear | 100 µg/ear | 50 µg/ear |
| 4c[b] | CH | CH | H | H | H | $CH_3$ | H | −84.9 ± 2.4 | −63.7 ± 3.9 | −52.8 ± 6.4 |
| 4d | CH | CH | H | H | $CH_3$ | $CH_3$ | H | −35.9 ± 7.4 | −27.8 ± 3.6 | −18.3 ± 3.3 |
| 4i | CH | CH | H | H | —(CH=CH)$_2$— | | H | — | −20.4 ± 2.1 | — |
| 4l | CH | CH | Br | H | —(CH=CH)$_2$— | | H | −30.6 ± 2.2 | −42.2 ± 3.1 | — |
| 4r | N | CH | H | H | —(CH=CH)$_2$— | | H | −29.0 ± 1.8 | −40.0 ± 1.9 | — |
| 4s | N | $CCH_3$ | H | $CH_3$ | $CH_3$ | $CH_3$ | H | — | −33.9 ± 3.9 | −17.3 ± 1.1 |
| 4t | N | $CCH_3$ | H | $CH_3$ | —(CH=CH)$_2$— | | H | — | — | −3.3 ± 1.6 |
| MK-886[c] (FLAP inhib.) | | | | | | | | −25.7 ± 8.1 | — | — |
| Indomethacin (CO inhib.) | | | | | | | | −26.6 ± 7.3 | — | — |

[a]Percent inhibition of AA-induced ear inflammation in mice; n = 10 animals per experimental group.
[b]Topical application $ED_{50}$ = 59.99 ± 0.03. Addition of 4c (100 µg) and indomethacin (250 µg) produced −86.84 ± 2.0 inhibition.
[c]MD-886 (3-[3-t-Butylthio-l-(p-chlorobenzyl)-5-isopropylindol-2-yl]-2,2-dimethylpropionic acid), reference 16.

The complete disclosures of all references cited in this specification are hereby incorporated by reference. Also, incorporated by reference is N. G. Bazan Carlos Sunkel, and Julio Alvarez-Builla, "(2-Azinylamino)quinone Derivatives as 5-Lipoxygenase Inhibitors," a manuscript to be submitted to J. Med. Chem. In the event of an otherwise irreconcilable conflict, however, the present specification shall control.

We claim:

1. A compound having the structure

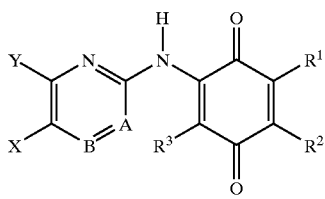

or a pharmaceutically acceptable salt thereof, wherein:
A is N, CH, or, CCl;
B is N, CH, $CCH_3$, or Cph;
X is H, Cl, Br, or I;
Y is H or $CH_3$;
$R^1$ is H; $CH_3$, $OCH_3$, or Ph; and $R^2$ is H, $CH_3$, $OCH_3$, or Ph; and
$R^3$ is H or $CH_3$.

2. The compound of claim 1 which is 2-Methyl-6-(pyridin-2-ylamino)-[1,4]benzoquinone (4b), or a pharmaceutically acceptable salt thereof.

3. The compound of claim 1 which is 2,3-Dimethyl-5-(pyridin-2-ylamino)-[1,4]benzoquinone (4d), or a pharmaceutically acceptable salt thereof.

9. The compound of claim 1 which is 2,3-Dimethoxy-5-methyl-6-(pyrimidin-2-ylamino)-[1,4]benzoquinone (4q), or a pharmaceutically acceptable salt thereof.

10. The compound of claim 1 which is 2,3-Dimethyl-5-(4,6-dimethylpyrimidin-2-ylamino)-[1,4]benzoquinone (4s), or a pharmaceutically acceptable salt thereof.

11. The compound of claim 1 which is 2-Methyl-6-(pyrazin-2-ylamino)-[1,4]benzoquinone (4v), or a pharmaceutically acceptable salt thereof.

12. A pharmaceutical composition comprising an amount of a compound of claim 1, or a pharmaceutically acceptable salt thereof, effective to inhibit 5-lipoxygenase, and a pharmaceutically acceptable carrier.

13. A method of inhibiting 5-lipoxygenase which comprises administering to a mammal an effective amount of a compound as recited in claim 1.

14. A compound having the structure

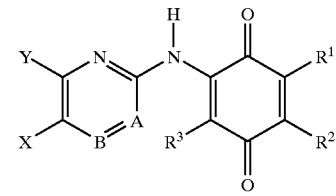

or a pharmaceutically acceptable salt thereof, wherein:
A is N, CH, or, CCl;
B is N, CH, $CCH_3$, or Cph;
X is H, Cl, Br, or I;
Y is H or $CH_3$;

$R^1$ is H; and $R^2$ is $CH_3$, $OCH_3$, or Ph; and $R^3$ is H or $CH_3$.

15. The compound of claim 14 which is 2-Methyl-5-(pyridin-2-ylamino)-[1,4]benzoquinone (4c), or a pharmaceutically acceptable salt thereof.

16. The compound of claim 14 which is 2-Methyl-5-(pyrimidin-2-ylamino)-[1,4]benzoquinone (4p), or a pharmaceutically acceptable salt thereof.

17. The compound of claim 14 which is 2-Methyl-5-(pyrazin-2-ylamino)-[1,4]benzoquinone (4x), or a pharmaceutically acceptable salt thereof.

18. A pharmaceutical composition comprising an amount of a compound of claim 14, or a pharmaceutically acceptable salt thereof, effective to inhibit 5-lipoxygenase, and a pharmaceutically acceptable carrier.

19. A method of inhibiting 5-lipoxygenase which comprises administering to a mammal an effective amount of a compound as recited in claim 14.

20. A compound having the structure

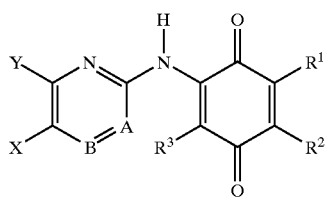

or a pharmaceutically acceptable salt thereof, wherein:

A is CH;

B is N, CH, $CCH_3$, or Cph;

X is H, Cl, Br, or I;

Y is H or $CH_3$;

$R^1$—$R^2$ is $(CH=CH)_2$; and $R^3$ is $CH_3$.

21. The compound of claim 20 which is 2-Methyl-3-(pyridin-2-ylamino)-[1,4]naphthoquinone (4j), or a pharmaceutically acceptable salt thereof.

22. A pharmaceutical composition comprising an amount of a compound of claim 20, or a pharmaceutically acceptable salt thereof, effective to inhibit 5-lipoxygenase, and a pharmaceutically acceptable carrier.

23. A method of inhibiting 5-lipoxygenase which comprises administering to a mammal an effective amount of a compound as recited in claim 20.

24. A compound having the structure

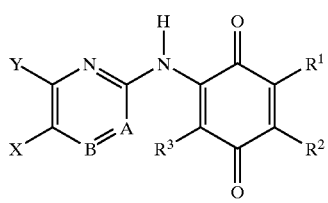

or a pharmaceutically acceptable salt thereof, wherein:

A is N or CCl;

B is N, CH, $CCH_3$, or Cph;

X is H, Cl, Br, or I;

Y is H or $CH_3$;

$R^1$—$R^2$ is $(CH=CH)_2$; and $R^3$ is H or $CH_3$.

25. The compound of claim 24 which is 2-(3,5-Dichloropyridin-2-ylamino)-[1,4]naphthoquinone (4n), or a pharmaceutically acceptable salt thereof.

26. The compound of claim 24 which is 2-(Pyrimidin-2-ylamino)-[1,4]naphthoquinone (4r), or a pharmaceutically acceptable salt thereof.

27. The compound of claim 24 which is 2-(4,6-Dimethylpyrimidin-2-ylamino)-[1,4]naphthoquinone (4t), or a pharmaceutically acceptable salt thereof.

28. The compound of claim 24 which is 2-(4-Phenylpyrimidin-2-ylamino)-[1,4]naphthoquinone (4u), or a pharmaceutically acceptable salt thereof.

29. A pharmaceutical composition comprising an amount of a compound of claim 24, or a pharmaceutically acceptable salt thereof, effective to inhibit 5-lipoxygenase, and a pharmaceutically acceptable carrier.

30. A method of inhibiting 5-lipoxygenase which comprises administering to a mammal an effective amount of a compound as recited in claim 24.

31. A compound having the structure

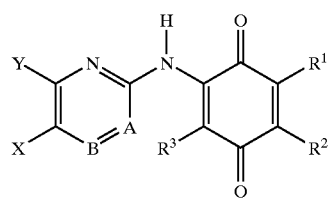

or a pharmaceutically acceptable salt thereof, wherein:

A is CH;

B is CH;

X is Cl, Br, or I;

Y is H or $CH_3$;

$R^1$—$R^2$ is $(CH=CH)_2$; and $R^3$ is H.

32. The compound of claim 31 which is 2-(5-Choropyridin-2-ylamino)-[1,4]naphthoquinone (4k), or a pharmaceutically acceptable salt thereof.

33. The compound of claim 31 which is 2-(5-Bromopyridin-2-ylamino)-[1,4]naphthoquinone (4l), or a pharmaceutically acceptable salt thereof.

34. The compound of claim 31 which is 2-(5-Iodopyridin-2-ylamino)-[1,4]naphthoquinone (4m), or a pharmaceutically acceptable salt thereof.

35. A pharmaceutical composition comprising an amount of a compound of claim 31, or a pharmaceutically acceptable salt thereof, effective to inhibit 5-lipoxygenase, and a pharmaceutically acceptable carrier.

36. A method of inhibiting 5-lipoxygenase which comprises administering to a mammal an effective amount of a compound as recited in claim 31.

37. A compound having the structure

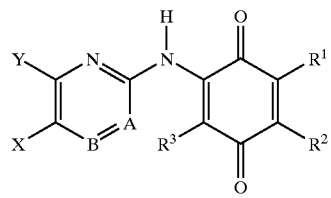

or a pharmaceutically acceptable salt thereof, wherein:

A is CH;

B is N, $CCH_3$, or Cph;

X is H, Cl, Br, or I;

Y is H or $CH_3$;

$R^1$—$R^2$ is $(CH=CH)_2$; and $R^3$ is H.

38. The compound of claim 37 which is 2-(Pyrazin-2-ylamino)-[1,4]naphthoquinone (4y), or a pharmaceutically acceptable salt thereof.

39. A pharmaceutical composition comprising an amount of a compound of claim 37, or a pharmaceutically acceptable salt thereof, effective to inhibit 5-lipoxygenase, and a pharmaceutically acceptable carrier.

40. A method of inhibiting 5-lipoxygenase which comprises administering to a mammal an effective amount of a compound as recited in claim 37.

41. A pharmaceutical composition comprising an amount of a compound which is 2-(Pyridin-2-ylamino)-[1,4]benzoquinone (4a), or a pharmaceutically acceptable salt thereof, effective to inhibit 5-lipoxygenase, and a pharmaceutically acceptable carrier.

42. A method of inhibiting 5-lipoxygenase which comprises administering to a mammal an effective amount of a compound which is 2-(Pyridin-2-ylamino)-[1,4]benzoquinone (4a), or a pharmaceutically acceptable salt thereof.

43. A pharmaceutical composition comprising an amount of a compound which is 2-(Pyridin-2-ylamino)-[1,4]naphthoquinone (4i), or a pharmaceutically acceptable salt thereof, effective to inhibit 5-lipoxygenase, and a pharmaceutically acceptable carrier.

44. A method of inhibiting 5-lipoxygenase which comprises administering to a mammal an effective amount of a compound which is 2-(Pyridin-2-ylamino)-[1,4]naphthoquinone (4i), or a pharmaceutically acceptable salt thereof.

* * * * *

UNITED STATES PATENT AND TRADEMARK OFFICE
CERTIFICATE OF CORRECTION

PATENT NO. : 6,653,311 B1
APPLICATION NO. : 10/179534
DATED : November 25, 2003
INVENTOR(S) : Nicolas G. Bazan et al.

It is certified that error appears in the above-identified patent and that said Letters Patent is hereby corrected as shown below:

In Column 11, lines 17 to 26, please replace structure 4e as shown:

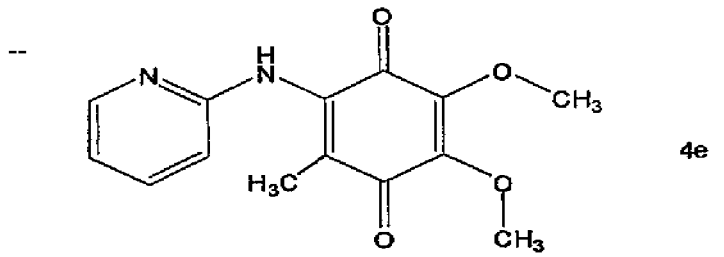

In Column 12, lines 33 to 42, please replace structure 4g as shown:

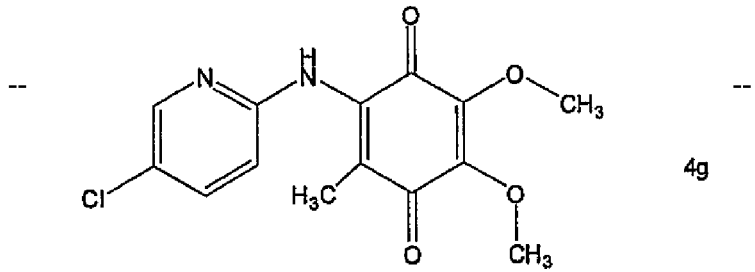

In Column 13, lines 5 to 15, please replace structure 4h as shown:

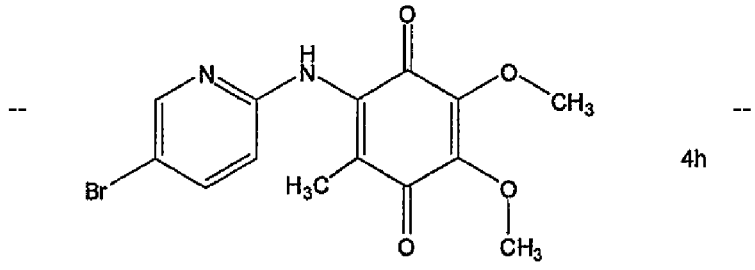

In Column 14, line 3, please correct line 3 to read:
--Quantitative Analysis. Calculated for $C_{15}H_{10}N_2O_2$.--

UNITED STATES PATENT AND TRADEMARK OFFICE
CERTIFICATE OF CORRECTION

PATENT NO.       : 6,653,311 B1
APPLICATION NO. : 10/179534
DATED            : November 25, 2003
INVENTOR(S)      : Nicolas G. Bazan et al.

It is certified that error appears in the above-identified patent and that said Letters Patent is hereby corrected as shown below:

In Column 19, lines 25 to 35, please replace structure 4s as shown:

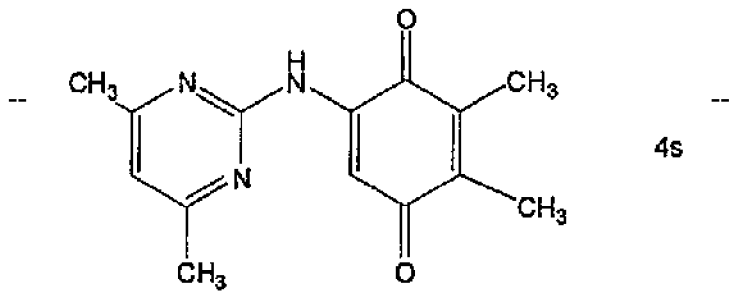

Signed and Sealed this

Sixteenth Day of October, 2007

JON W. DUDAS
*Director of the United States Patent and Trademark Office*